US012754165B2

(12) United States Patent
Cruzado-Park

(10) Patent No.: US 12,754,165 B2
(45) Date of Patent: Oct. 6, 2026

(54) METHODS AND COMPOSITIONS FOR ELECTOPHORETIC SEPARATIONS

(71) Applicant: DH Technologies Development Pte. Ltd., Singapore (SG)

(72) Inventor: Ingrid D. Cruzado-Park, Brea, CA (US)

(73) Assignee: DH Techologies Development Pte. Ltd., Singapore (SG)

( * ) Notice: Subject to any disclaimer, the term of this patent is extended or adjusted under 35 U.S.C. 154(b) by 215 days.

(21) Appl. No.: 18/742,865

(22) Filed: Jun. 13, 2024

(65) Prior Publication Data

US 2024/0426779 A1 Dec. 26, 2024

Related U.S. Application Data

(60) Provisional application No. 63/509,122, filed on Jun. 20, 2023.

(51) Int. Cl.
*G01N 27/447* (2006.01)
*C07K 1/28* (2006.01)

(52) U.S. Cl.
CPC ......... *G01N 27/44795* (2013.01); *C07K 1/28* (2013.01)

(58) Field of Classification Search
CPC ............................ G01N 27/44795; C07K 1/28
See application file for complete search history.

(56) References Cited

U.S. PATENT DOCUMENTS

| | | | | |
|---|---|---|---|---|
| 4,401,538 A * | 8/1983 | Hausfeld | G01N 27/44795 204/644 |
| 2015/0162177 A1* | 6/2015 | McGivney | G01N 27/44795 250/288 |
| 2025/0003922 A1* | 1/2025 | Elnaggar | G16B 40/10 |

OTHER PUBLICATIONS

Suba et al., "Capillary isoelectric focusing method development and validation for investigation of recombinant therapeutic monoclonal antibody," Journal of Pharmaceutical and Biomedical Analysis 114 (2015) 53-61 (Year: 2015).*

Millipore-Sigma product literature for Pharmalyte® 3-10, downloaded Mar. 11, 2026 from https://www.sigmaaldrich.com/US/en/product/sigma/ge17045601?srsltid=AfmBOoptzHcoLJEs7z4oxCJrODjiTSqn7ycwyc9t827w6eDrXSdUduZn (Year: 2026).*

Lillard et al., "Analysis of single erythrocytes by injection-based capillary isoelectric focusing with laser-induced native fluorescence detection," Journal of Chromatography B, 687 (1996) 363-369 (Year: 1996).*

(Continued)

*Primary Examiner* — Alexander S Noguerola
(74) *Attorney, Agent, or Firm* — Lathrop GPM LLP; Malaika O.D. Tyson; Jason Kuchar

(57) ABSTRACT

Disclosed and claims are a method for analyzing at least one analyte, the method including introducing a composition into a separation channel, wherein the composition includes at least one pH gradient compound, an amine buffer, and at least one analyte of interest; applying an electric field across the separation channel to create a pH gradient using the at least one pH gradient compound and separate the composition via isoelectric focusing, generating at least one focused analyte peak; mobilizing the at least one focused analyte peak; and wherein the amine buffer is configured to modify the pH gradient.

15 Claims, 13 Drawing Sheets

(56) References Cited

OTHER PUBLICATIONS

NIH National Library of Medicine—PubChem information sheet about the compound Tris(hydroxymethyl)aminomethane , downloaded Mar. 11, 2026 from https://pubchem.ncbi.nlm.nih.gov/compound/Tris_hydroxymethyl_aminomethane#section=Ionization-Efficiency (Year: 2026).*

Zhang et al., Mass spectrometry for the biophysical characterization of therapeutic monoclonal antibodies, FEBS Letters 588 (2014) 308-317 (Year: 2014).*

Cao et al., "Charge profiling and stability testing of biosimilar by capillary isoelectric focusing," Electrophoresis 2014, 35, 1461-1468 (Year: 2014).*

Wu et al., "Capillary Isoelectric Focusing Methods for Charge-based Analysis of Biotech Pharmaceutical Samples," Chapter 26 in Bioseparation and Bioprocessing—A Handbook, vol. 2, ed. Ganapathy Subramanian, 2nd edition, Wiley-VCH Verlag GmbH & Co. KGaA, 2007 (Year: 2007).*

* cited by examiner

METHODS AND COMPOSITIONS FOR ELECTOPHORETIC SEPARATIONS

RELATED APPLICATIONS

The present patent application claims the priority benefit of U.S. Provisional Patent Application Ser. No. 63/509,122, filed Jun. 20, 2023, the content of which is hereby incorporated by reference in its entirety into this disclosure.

BACKGROUND

In isoelectric focusing, a sample, such as a protein sample, is mixed with an ampholyte solution. This sample/ampholyte solution is then transferred into a channel (e.g., a separation channel in a fluidic device, a capillary, or a capillary channel). One end of the channel is then connected to an anolyte solution (e.g., an acidic solution) and the other end is connected to a catholyte solution (e.g., a basic solution). A high voltage is applied across the channel, causing ion migration and, as a result, establishing a pH gradient across the channel. At the same time, components of the sample (e.g., a protein) will also migrate toward the region along the length of the channel where the local pH is the closest to the component's isoelectric point (pI). When, e.g., the protein reaches its pI, it will have a net zero charge and will stop migrating. This step is called "focusing." An image of the channel after, e.g., all proteins in the sample reach their pIs may show the relative abundance of the various protein species in the sample. The pI of the various protein species can be determined by their relative position to pI markers that are added to the sample solution. Following the completion of the separation, the focused sample may be re-ionized and transported (e.g., electrokinetically) e.g., for downstream analysis. This step is called "mobilizing" or "mobilization," and the process must preserve the spatial separation of the focused species.

Isoelectric separations often employ cathodic and anodic stabilizers to protect the pH gradient from distortions. A cathodic stabilizer will fill the portion of the capillary from detector to outlet and force the formation of the gradient before the detection window. The anodic stabilizer is used to minimize distortions on the pH gradient at the anodic side, maximizing resolution while preventing the loss of sample into the anolyte vial. Generally, an anodic stabilizer is a high-conductivity molecule that has a pI value lower than the ampholytes but above the pH of the anolyte.

The recommended anodic stabilizer, iminodiacetic acid (IDA) has low solubility. It has a tendency to precipitate at high concentrations and can precipitate at low temperatures. Once IDA precipitates inside the capillary, it is difficult to redissolve due to its low solubility. Precipitation leads to premature failure of capillary coatings, and IDA precipitate interferes with separation resolution and reproducibility, as well as downstream mass spectrometry. At the capillary inlet, where IDA may be focused into a small volume, it can precipitate leading to capillary plugging, thus reducing the capillary run-life.

SUMMARY

Disclosed herein is a method that enables improved separation and analysis of analytes in an analyte mixture, with potential applications in biomedical research, clinical diagnostics, and pharmaceutical manufacturing. In particular, the addition of an amine buffer configured to modify the pH gradient increases the design space for cIEF (capillary isoelectric focusing) assays by allowing a very wide selection of anodic stabilizers on the basis of the desired pH limit for the gradient. Thus, it is possible to choose the lower limit of pH in a cIEF experiment by selection of a suitable acid having a pKa equal to the lower limit. In addition, acids are generally more soluble and less likely to precipitate than ampholytic blockers, and the use of volatile acids as anodic stabilizer would be compatible with mass spectrometry as detector for cIEF-MS.

One aspect of the disclosure is a method for analyzing at least one analyte, the method including introducing a composition into a separation channel, wherein the composition includes at least one pH gradient compound, an amine buffer, and at least one analyte of interest; applying an electric field across the separation channel to create a pH gradient using the at least one pH gradient compound and separate the composition via isoelectric focusing, generating at least one focused analyte peak; mobilizing the at least one focused analyte peak; and wherein the amine buffer is configured to modify the pH gradient.

In an aspect, the method includes analyzing at least two analytes; alternatively at least three analytes; alternatively at least four analytes; alternatively at least five analytes; alternatively at least six analytes; alternatively at least seven analytes; alternatively at least eight analytes; alternatively at least nine analytes; or alternatively at least ten analytes.

In an aspect, modification of the pH gradient comprises adjusting the pH gradient's linearity. In an aspect, the pH gradient is non-linear. In another aspect, the modification of the pH gradient results in a shallow pH gradient. In an aspect, the modification of the pH gradient results in improvements in characterization of the at least one analyte. In another aspect, the improvement in characterization of the at least one analyte includes improved separation of the at least one analyte compared to that attained in a method which does not comprise the amine buffer.

In an aspect, the amine buffer has a pKa of about 6.0 to about 8.5. In an aspect, the composition has a concentration of amine buffer of about 2.5 mM, alternatively about 5.0 mM, alternatively about 10 mM, alternatively about 20 mM, alternatively about 30 mM, alternatively about 40 mM, alternatively about 50 mM, alternatively about 60 mM, alternatively about 70 mM, alternatively about 80 mM, alternatively about 90 mM, alternatively about 0.1 M, alternatively about 0.25 M, alternatively about 0.5 M, alternatively about 0.75 M, alternatively about 1.0 M, alternatively about 1.25 M, alternatively about 1.5 M, alternatively about 1.75 M, alternatively about 2 M.

In an aspect, the amine buffer is selected from the group consisting of Tris, Bis-Tris, HEPES, MES, PIPES, TES, dimethylamine, and combinations thereof. In an aspect, the at least one analyte has a pI of between about 7.0 and about 9.5.

In an aspect, the at least one analyte is a biomolecule. In another aspect, the biomolecule is a protein, a peptide, an amino acid, an antibody, or combinations thereof. In yet another aspect, the biomolecule comprises at least two isoforms and the method improves the characterization of the at least two isoforms.

In an aspect, the at least one pH gradient compound is at least one amphoteric compound. In another aspect, the at least one amphoteric compound is at least one carrier ampholyte.

In an aspect, the method further includes introducing a polymer solution, an anodic stabilizer, a cathodic stabilizer, and/or a pI marker into the separation channel. In an aspect, the anodic stabilizer comprises a carboxylic acid. In an aspect, the anodic stabilizer comprises acetic acid or iminodiacetic acid.

In an aspect, the at least one focused analyte peak is mobilized using pressure or a chemical mobilizer. In an aspect, the anodic stabilizer is used as a chemical mobilizer. In another aspect, the cathodic stabilizer comprises arginine.

In an aspect, the method further includes imaging the separation channel or a portion thereof during or after the isoelectric focusing separation and/or mobilization. In an aspect, imaging the separation channel or a portion thereof is used to generate image data.

In an aspect, the method further includes expelling the at least one mobilized analyte peak into a mass spectrometer. In an aspect, the method further includes generating mass spectrometry data. In an aspect, the method further includes correlating the at least one analyte peak detected by imaging of the separation channel or a portion thereof with mass spectrometry data for the at least one separated analyte.

In an aspect, the method further includes generating a corresponding set of values from the image data and/or mass spectrometry data, wherein the corresponding set of values is used to generate a calibration curve. In an aspect, the calibration curve is a linear or non-linear calibration curve. In an aspect, the calibration curve is used to determine the pI value of an unkno

BRIEF DESCRIPTION OF FIGURES

Various aspects of the present disclosure will now be described, by way of example only, with reference to the attached Figures, wherein.

DETAILED DESCRIPTION

Figure 1A:
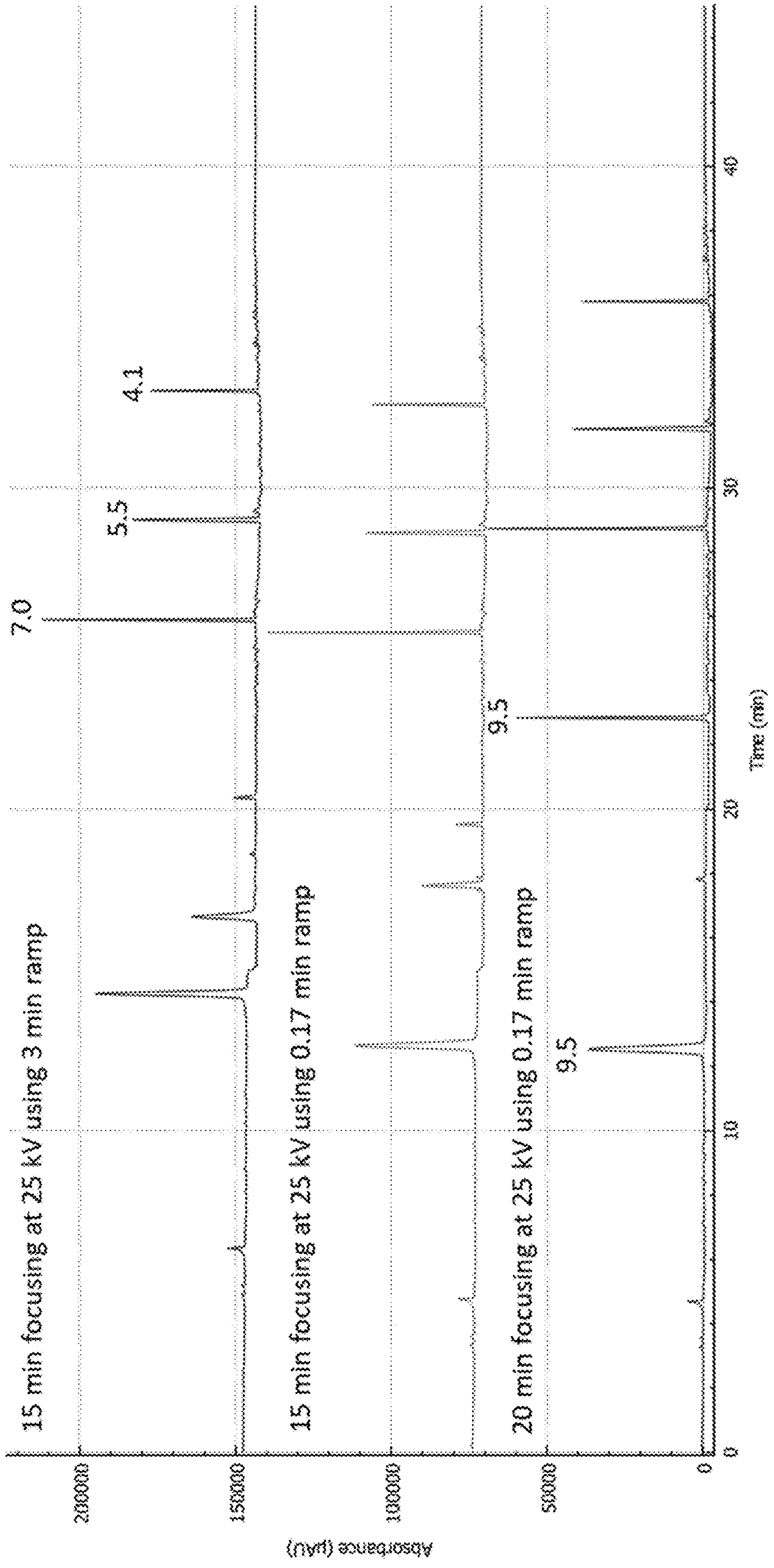
FIG. 1A shows a cIEF separation according to an aspect of this disclosure of 10 μL Tris in a cIEF composition including 200 μL cIEF gel, 12 μL of Pharmalyte 3-10, 2 μL of each pI marker using 15 min focusing at 25 kV using 3 min ramp (top graph), 15 min focusing at 25 kV using 0.17 min ramp (middle graph), and 20 min focusing at 25 kV using 0.17 min ramp (bottom graph).

Unless otherwise defined, all technical and scientific terms used herein have the same meaning as commonly understood by one of ordinary skill in the art to which the methods described herein belong. Any reference to standard methods (e.g., ASTM, TAPPI, AATCC, etc.) refers to the most recent available version of the method at the time of filing of this disclosure unless otherwise indicated.

For any method disclosed herein that includes discrete steps, the steps may be conducted in any feasible order. In addition, as appropriate, any combination of two or more steps may be conducted simultaneously.

All headings are for the convenience of the reader and should not be used to limit the meaning of the text that follows the heading, unless so specified.

The words "preferred" and "preferably" refer to aspects of the invention that may afford certain benefits, under certain circumstances. However, other aspects may also be preferred, under the same or other circumstances. Furthermore, the recitation of one or more preferred aspects does not imply that other aspects are not useful and is not intended to exclude other aspects from the scope of the invention.

The term "comprises" and variations thereof do not have a limiting meaning where these terms appear in the description and claims. Such terms will be understood to imply the inclusion of a stated step or element or group of steps or elements but not the exclusion of any other step or element or group of steps or elements.

By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

The singular form "a", "an" and "the" include plural referents unless the context clearly dictates otherwise. These articles refer to one or to more than one (i.e., to at least one). As used herein, the term "or" is generally employed in its usual sense including "and/or" unless the content clearly dictates otherwise. The term "and/or" means any one or more of the items in the list joined by "and/or". As an example, "x and/or y" means any element of the three-element set {(x), (y), (x, y)}. In other words, "x and/or y" means "one or both of x and y". As another example, "x, y, and/or z" means any element of the seven-element set {(x), (y), (z), (x, y), (x, z), (y, z), (x, y, z)}. In other words, "x, y and/or z" means "one or more of x, y and z".

Where ranges are given, endpoints include all numbers subsumed within that range (e.g., 1 to 5 includes 1, 1.5, 2, 2.75, 3, 3.80, 4, 5, etc.). Furthermore, unless otherwise indicated or otherwise evident from the context and understanding of one of ordinary skill in the art, values that are expressed as ranges can assume any specific value or subrange within the stated ranges in different aspects of the disclosure, to the tenth of the unit of the lower limit of the range, unless the context clearly dictates otherwise. Herein, "up to" a number (for example, up to 50) includes the number (for example, 50). The term "in the range" or "within a range" (and similar statements) includes the endpoints of the stated range.

Reference throughout this specification to "one aspect," "an aspect," "certain aspects," or "some aspects," etc., means that a particular feature, configuration, composition, or characteristic described in connection with the aspect is included in at least one aspect of the disclosure. Thus, the appearances of such phrases in various places throughout this specification are not necessarily referring to the same aspects of the disclosure. Furthermore, the particular features, configurations, compositions, or characteristics may be combined in any suitable manner in one or more aspects.

Unless otherwise indicated, all numbers expressing quantities of components, molecular weights, and so forth used in the specification and claims are to be understood as being modified in all instances by the term "about." As used herein in connection with a measured quantity, the term "about" refers to that variation in the measured quantity as would be expected by the skilled artisan making the measurement and exercising a level of care commensurate with the objective of the measurement and the precision of the measuring equipment used. The term "about" as used in connection with a numerical value throughout the specification and the claims denotes an interval of accuracy, familiar and acceptable to a person skilled in the art. In general, such interval of accuracy is +/−10%. Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

The term "exemplary" means serving as a non-limiting example, instance, or illustration. As utilized herein, the terms "e.g." and "for example" set off lists of one or more non-limiting aspects, examples, instances, or illustrations.

As used herein, the term "substantially" refers to the qualitative condition of exhibiting total or near-total extent or degree of a characteristic or property of interest. Biological and chemical phenomena rarely, if ever, go to completion and/or proceed to completeness or achieve or avoid an absolute result. The term "substantially" is therefore used herein to capture the potential lack of completeness inherent in many biological and chemical phenomena. For example, "substantially" may refer to being within at least about 20%, alternatively at least about 10%, or alternatively at least about 5% of a characteristic or property of interest.

The invention is defined in the claims. However, below is a non-exhaustive listing of non-limiting exemplary aspects. Any one or more of the features of these aspects may be combined with any one or more features of another example, embodiment, or aspect described herein.

One aspect of the disclosure is a method for analyzing at least one analyte. In some examples, the method includes introducing a compound into a separation channel. The separation channel may be a part of a fluidic device, including, but not limited to microfluidic and nanofluidic devices. The separation channel may be part of a capillary, including but not limited to, capillary electrophoresis (CE) systems. The method may be an electrophoretic separation, including but not limited to CE, capillary zone electrophoresis (CZE), capillary gel electrophoresis (CGE), capillary isoelectric focusing (cIEF), or imaged capillary isoelectric focusing (icIEF).

In an aspect, the composition includes at least one pH gradient compound, an amine buffer, and at least one analyte of interest. The pH gradient compound may be an amphoteric compound. Amphoteric compounds are compounds that can react as both an acid and base as the compound have at least two pKa values, at least one of which is acidic and at least one of which is basic. In non-limiting examples, the amphoteric compound is an ampholyte, such as a carrier ampholyte. In cIEF or icIEF, a mixture of carrier ampholytes with various pIs may be used. When an electric field is applied to the separation channel, the carrier ampholytes travel based on their pI, with the most acidic ampholyte traveling the furthest toward the anode. This generates a pH gradient whereby the carrier ampholyte with low pHs are closer to the anode and the carrier ampholytes with high pHs are closer to the cathode.

An isoelectric point (pI) marker, such as a protein or peptide pI marker may be added after the introduction of the composition or simultaneously with the composition. The pI marker may be used for external or internal standardization.

A polymer solution, an anodic stabilizer, and/or a cathodic stabilizer may also be added after the introduction of the composition or simultaneously with the composition. In some aspects, cIEF or icIEF require the addition of stabilizers to protect the pH gradient from isotachophoretic distortions caused by the introduction of anolyte and catholyte ions in the separation channel. A suitable stabilizer is a UV-transparent single chemical compound of high purity and conductivity, which has a pI value above or below the pH range of the ampholytes. Additionally, the cathodic stabilizer pI value must be less than the catholyte pH value, and the anodic stabilizer pI value must be greater than the anolyte pH value. In this manner, the stabilizers are forced to focus on the pH gradient ends inside the separation channel without falling into catholyte and anolyte vials.

In some non-limiting examples, the cathodic stabilizer includes arginine. In some non-limiting examples, the anodic stabilizer includes a carboxylic acid, such as acetic acid or iminodiacetic acid.

In an aspect of the method, an electric field may be applied across the separation channel to create a pH gradient using the at least one pH gradient compound. The electric field may also assist in the separation of the composition. The separation of compositions, using, for example, cIEF or icIEF, may be performed along the separation channel to spatially separate different charge-variant isoforms into distinct "bands", which can be observed as "peaks" via UV absorption detection. Following the completion of the separation, the pH gradient is disrupted and the focused sample components are moved toward the separation channel outlet. This process is known as mobilization. This mobilization method may be chemical, hydrodynamic (or pressure), or electroosmotic flow driven. In a chemical mobilization, a weak acid, such as a carboxylic acid, including, but not limited to acetic acid or iminodiacetic acid, may be used to disrupt the pH gradient.

In some aspects of the method, acetic acid is used as both the anodic stabilizer and chemical mobilizer. This provides several advantages including the high purity and high chemical stability of the acetic acids, as well as the solubility and lack of precipitation.

In an aspect of the method, the amine buffer is configured to modify the pH gradient. Often in cIEF or icIEF, the pH gradient is linear. In the disclosed method, the introduction of the amine buffer may adjust the pH gradient's linearity, for example, it may cause the pH gradient to be non-linear. In a non-limiting example, the amine buffer may be tris (hydroxymethyl)aminomethane (Tris), 2,2-Bis(hydroxymethyl)-2,2',2"-nitrilotriethanol (BIS-TRIS), 4-(2-Hydroxyethyl)piperazine-1-ethanesulfonic acid, N-(2-Hydroxyethyl) piperazine-N'-(2-ethanesulfonic acid) (HEPES), 2-(N-Morpholino) ethanesulfonic acid (MES), Piperazine-N,N'-bis(2-ethanesulfonic acid) (PIPES), 2-{[1,3-Dihydroxy-2-(hydroxymethyl)propan-2-yl]amino}ethane-1-sulfonic acid (TES), dimethylamine, or combinations thereof. The amine buffer may also have a pKa of about 6.0 to about 8.5.

In an exemplary aspect of the method, the modification of the pH gradient may result in a shallow pH gradient and/or improvements in characterization of the at least one analyte. The improvement in characterization of the at least one analyte includes improved separation of the at least one analyte compared to that attained in a method which does not comprise the amine buffer.

The composition may contain a concentration of amine buffer to allow for modification of the pH gradient. In a non-limiting example, the composition has a concentration of amine buffer of about 2.5 mM. In another non-limiting example, the composition has a concentration of amine buffer of about 5.0 mM. In another non-limiting example, the composition has a concentration of amine buffer of about 10 mM. In another non-limiting example, the composition has a concentration of amine buffer of about 20 mM. In another non-limiting example, the composition has a concentration of amine buffer of about 30 mM. In another non-limiting example, the composition has a concentration of amine buffer of about 40 mM. In another non-limiting example, the composition has a concentration of amine buffer of about 50 mM. In another non-limiting example, the composition has a concentration of amine buffer of about 60 mM. In another non-limiting example, the composition has a concentration of amine buffer of about 70 mM. In another non-limiting example, the composition has a concentration of amine buffer of about 80 mM. In another non-limiting example, the composition has a concentration of amine buffer of about 90 mM. In another non-limiting example, the composition has a concentration of amine buffer of about 0.1 M. In another non-limiting example, the composition has a concentration of amine buffer of about 0.25 M. In another non-limiting example, the composition has a concentration of amine buffer of about 0.5 M. In another non-limiting example, the composition has a concentration of amine buffer of about 0.75 M. In another non-limiting example, the composition has a concentration of amine buffer of about 1.0 M. In another non-limiting example, the composition has a concentration of amine buffer of about 1.25 M. In another non-limiting example, the composition has a concentration of amine buffer of about 1.5 M. In another non-limiting example, the composition has a concentration of amine buffer of about 1.75 M. In another non-limiting example, the composition has a concentration of amine buffer of about 2 M.

In an aspect of the method, the analyte is a biomolecule. Non-limiting examples include a protein, a peptide, an amino acid, an antibody, or combinations thereof. The analyte may also have a pI of between about 7.0 and about 9.5. In an aspect, the biomolecule includes at least two isoforms and the method improves the characterization of the at least two isoforms.

Depending on the analysis desired, the method may further include imaging the separation channel or a portion thereof during or after the isoelectric focusing separation and/or mobilization. An image of the channel after, e.g., all biomolecules in the sample reach their pIs may show the relative abundance of the various protein species in the sample. In some aspects, the images may be used to detect the presence of one or more markers or indicators, e.g., isoelectric point (pI) standards, within the separation channel and thus determine the pIs for the one or more analytes. In some aspects, the images may be used to detect a failure in a separation channel (e.g., bubble formation). In some aspects, data derived from such images may be used to determine when a separation reaction is complete (e.g., by monitoring peak velocities, peak positions, and/or peak widths) and subsequently trigger a mobilization step.

Once focusing is complete, mobilization may be initiated. Imaging of the separation channel may also occur while mobilizing is in process. Imaging of the separation channel may also occur after mobilizing is in process.

In some aspects, the mobilization of a series of one or more focused analytes may include causing the focused analytes to migrate towards a fluid outlet of the separation channel that is in fluid communication with a downstream analytical instrument. For example, the method may include analyzing at least two analytes, or alternatively at least three analytes, or alternatively at least four analytes, or alternatively at least five analytes, or alternatively at least six analytes, or alternatively at least seven analytes, or alternatively at least eight analytes, or alternatively at least nine analytes or alternatively at least ten analytes.

In some aspects, the fluid outlet may be in fluid communication with an electrospray ionization (ESI) interface such that the migrating analyte peaks are delivered into a mass spectrometer. In some aspects, the image data used to detect analyte peak positions and determine analyte pIs may also be used to correlate analyte separation data with mass spectrometry data. In some aspects, the image data used to detect analyte peak positions may be used to yield information on the mobilization reaction and/or to correlate the mobilization information with the mass spectrometry data.

One aspect of the method further includes using the image data and/or mass spectrometry data to generate a corresponding set of values. In non-limiting examples, these values may be used to generate a calibration curve. In some aspects, the calibration curve is a linear or non-linear calibration curve. In other aspects, the calibration curve is used to determine the pI value of an unkno The presently described technology and its advantages will be better understood by reference to the following examples. These examples are provided to describe specific implementations of the present technology. By providing these specific examples, it is not intended limit the scope and spirit of the present technology. It will be understood by those skilled in the art that the full scope of the presently described technology encompasses the subject matter defined by the claims appending this specification, and any alterations, modifications, or equivalents of those claims.

EXAMPLES

Exemplary cIEF Separation cIEF separations were carried out in a PA 800 plus Pharmaceutical Analysis System (SCIEX, Framingham, MA, USA) equipped with UV detection set at 280 nm. Separations were carried out in a 50 μm id, 375 μm od 20.0/30.2 cm long neutral-coated capillary (SCIEX) thermostated at 20° C. Samples were stored at 10° C. inside the system sample garage. The neutral-coated capillary was rinsed for 5 min at 70 psi with Neutral Capillary Conditioning Solution (SCIEX) before use and at the end of the separation sequence.

All chemicals were acquired from MilliporeSigma (Burlington, MA, USA), unless mentioned otherwise. cIEF gel and peptide pI markers (10.0, 9.5, 7.0, 5.5 and 4.1) were obtained from SCIEX. Peptide with pI 3.4 was synthesized by SynBioSci (Livermore, CA USA). Pharmalyte pH 3-10 carrier ampholytes were purchased from Cytiva (Marlborough, MA, USA). Double-deionized water was generated by Labconco WaterPro BT purification system (Kansas City, MO, USA), and it was used in the preparation of all solutions and in all procedure steps that require water.

Use of Tris to Modify a pH Gradient

Four cIEF samples were prepared by combining the following volumes 200 μL cIEF gel, 12 μL of Pharmalyte 3-10, 2 μL of each pI marker with four different volumes of 1.0 M Tris (10 μL, 15 μL, 20 μL, 25 μL). The samples were separated using the exemplary method.

Figure 1B:
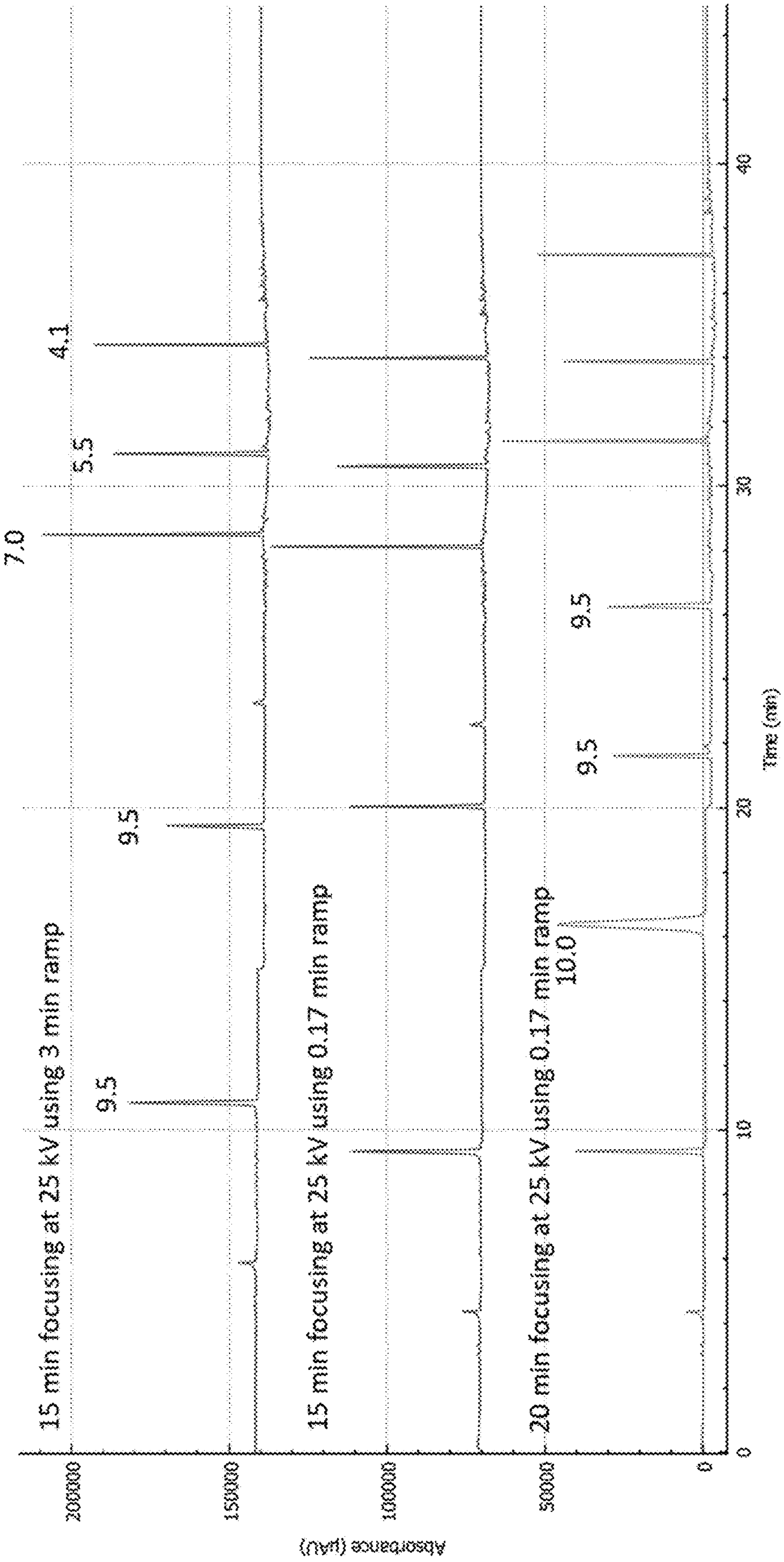
FIG. 1B shows a cIEF separation according to an aspect of this disclosure of 15 μL Tris in a cIEF composition including 200 μL cIEF gel, 12 μL of Pharmalyte 3-10, 2 μL of each pI marker using 15 min focusing at 25 kV using 3 min ramp (top graph), 15 min focusing at 25 kV using 0.17 min ramp (middle graph), and 20 min focusing at 25 kV using 0.17 min ramp (bottom graph).
Figure 1C:
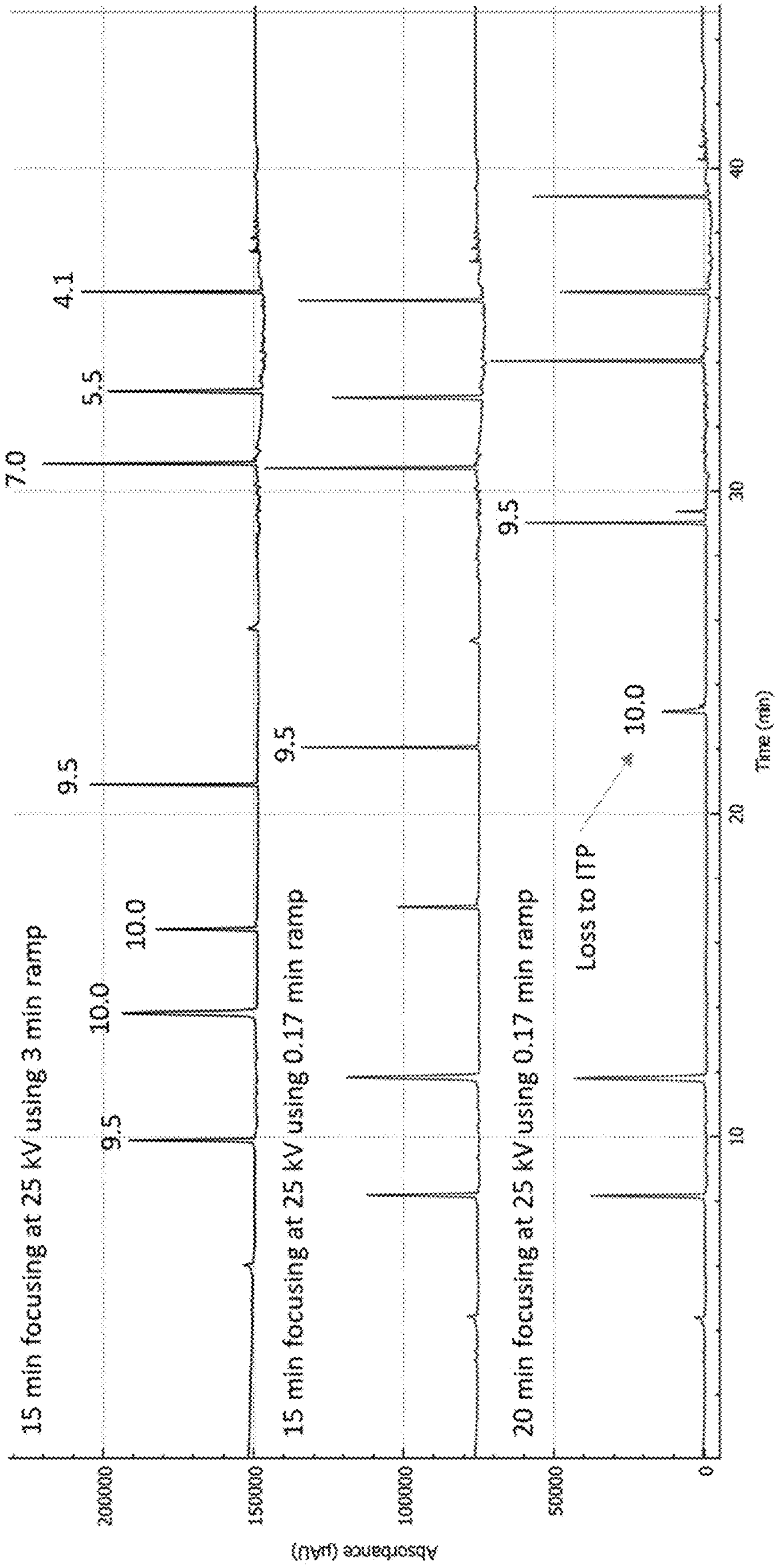
FIG. 1C shows a cIEF separation according to an aspect of this disclosure of 20 μL Tris in a cIEF composition including 200 μL cIEF gel, 12 μL of Pharmalyte 3-10, 2 μL of each pI marker using 15 min focusing at 25 kV using 3 min ramp (top graph), 15 min focusing at 25 kV using 0.17 min ramp (middle graph), and 20 min focusing at 25 kV using 0.17 min ramp (bottom graph).
Figure 1D:
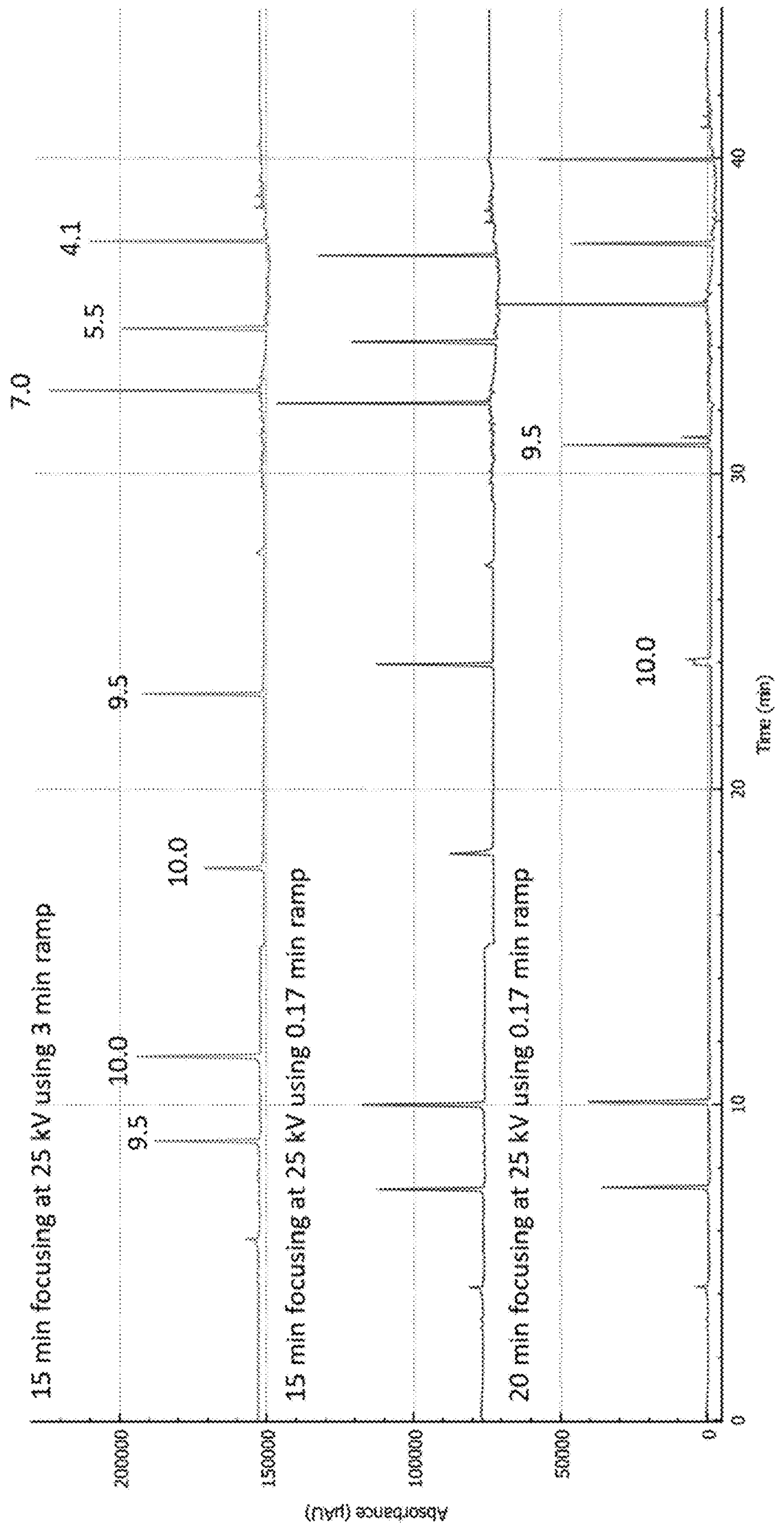
FIG. 1D shows a cIEF separation according to an aspect of this disclosure of 25 μL Tris in a cIEF composition including 200 μL cIEF gel, 12 μL of Pharmalyte 3-10, 2 μL of each pI marker using 15 min focusing at 25 kV using 3 min ramp (top graph), 15 min focusing at 25 kV using 0.17 min ramp (middle graph), and 20 min focusing at 25 kV using 0.17 min ramp (bottom graph).

FIG. 1A shows a cIEF separation with 10 μL Tris. FIG. 1B shows a cIEF separation with 15 μL Tris. FIG. 1C shows a cIEF separation with 20 μL Tris. FIG. 1D shows a cIEF separation with 25 μL Tris. Tris has a pKa of 8.1 and as shown in FIGS. 1A-1D, the pH gradient is pushed towards higher detection times as the concentration of Tris is increased in the sample sets. The pH gradient is also wider between pI 9.5 and pI 10. As shown in FIG. 1A, the when a 15 min focusing at 25 kV using 0.17 min ramp is employed, the resulting focusing area between pI 9.5 and pI 10 is increased. Similar results can be seen in FIGS. 1B-1D. Duplicative pIs in some of the traces of FIGS. 1A-1D may indicate the marker is not fully focused or one pI peak is formed during focusing and the other during mobilization. Various conditions, including increasing the concentration of Tris, are employed to help fully focus the marker.

Figure 1E:
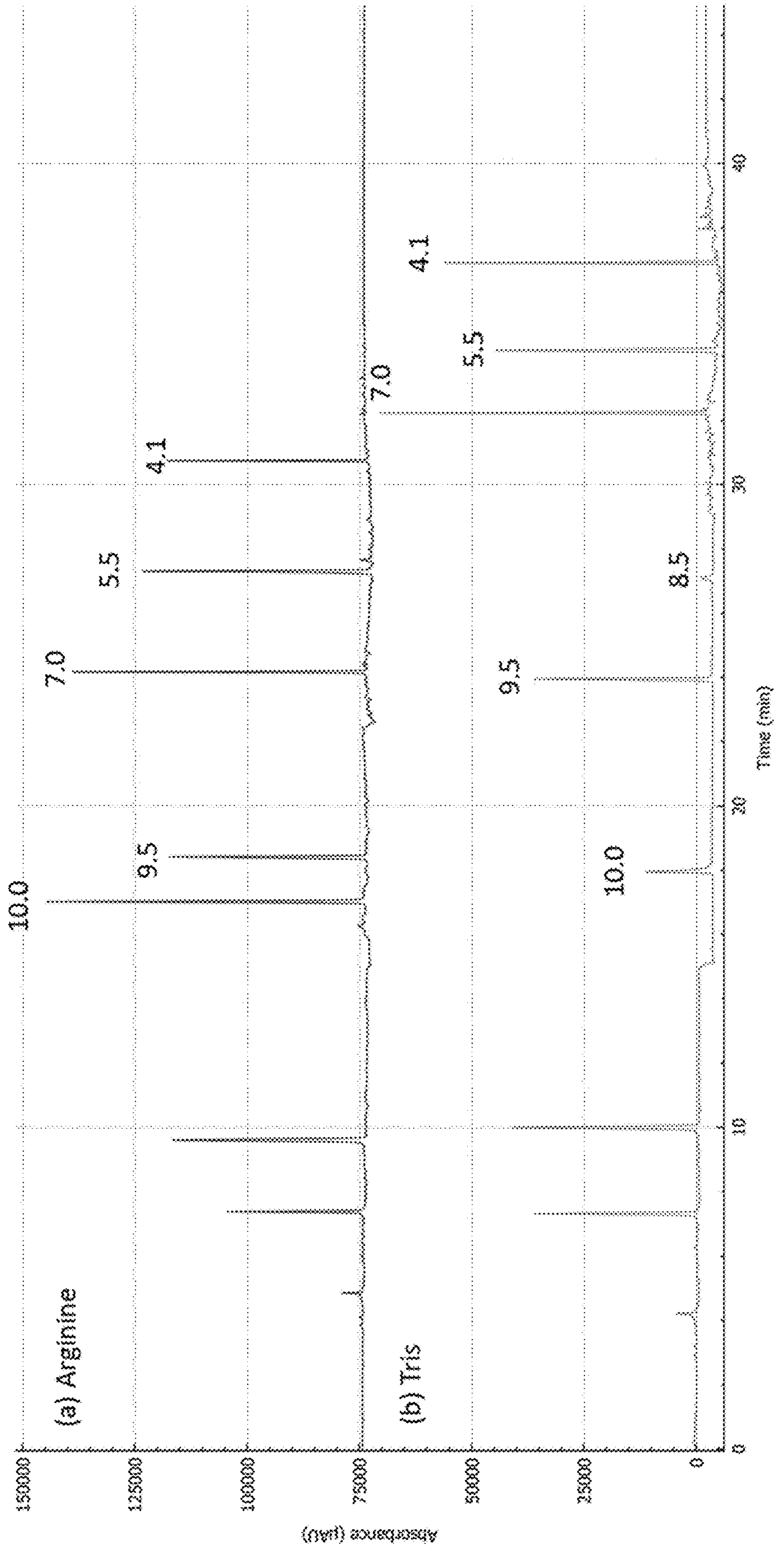
FIG. 1E shows a comparison of a cIEF separation according to an aspect of this disclosure of peptide pI markers with arginine (top graph) and Tris (bottom graph).

FIG. 1E is a comparison of a cIEF separation with two amine buffers—arginine and Tris—according to the exemplary method. As shown, not only is the pH gradient shifted towards higher detection times, the pH gradient is widened, allowing for better resolution of analytes between the pIs of 9.5 and 10. The use of Tris also increases sensitivity, as the baseline is flatter than in the arginine run.

Use of Tris in a cIEF Separation of Protein Isoforms cIEF compositions were prepared by combining the following volumes 300 μL cIEF gel, 18 μL of Pharmalyte 3-10, 3.0 μL of each pI marker, and 13.5 μL of NIST IgG. To prepare a cIEF sample with arginine, 12.5 μL of arginine was added to 115.5 μL of the cIEF composition. To prepare a cIEF sample with Tris, 12.5 μL of 1.0M Tris was added to 115.5 μL of the cIEF composition. The samples were separated using the exemplary method.

Figure 2A:
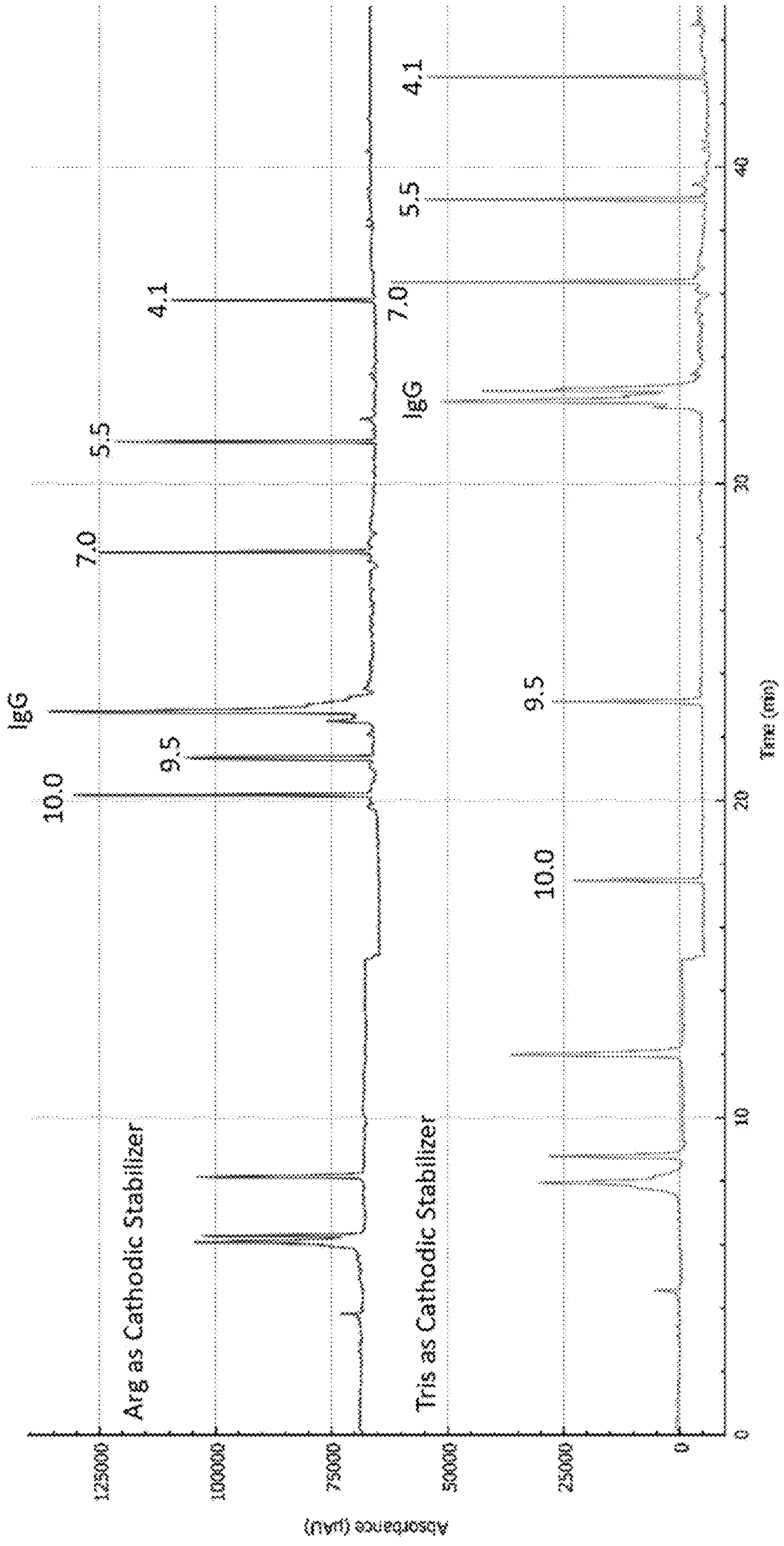
FIG. 2A shows a comparison of a cIEF separation according to an aspect of this disclosure of IgG with arginine (top graph) and Tris (bottom graph).
Figure 2B:
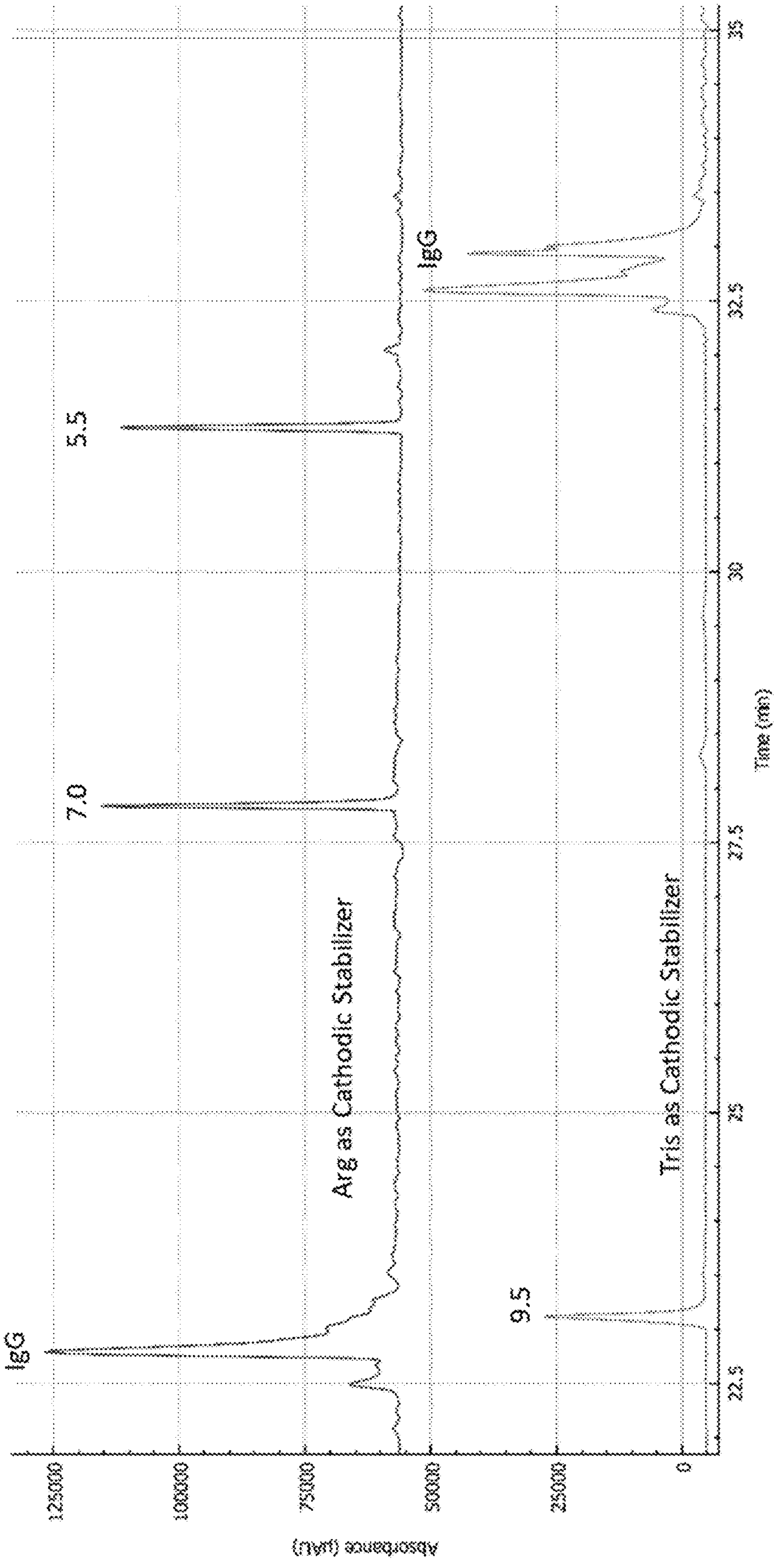
FIG. 2B shows a comparison of a cIEF separation according to an aspect of this disclosure of IgG with arginine (top graph) and Tris (bottom graph).
Figure 2C:
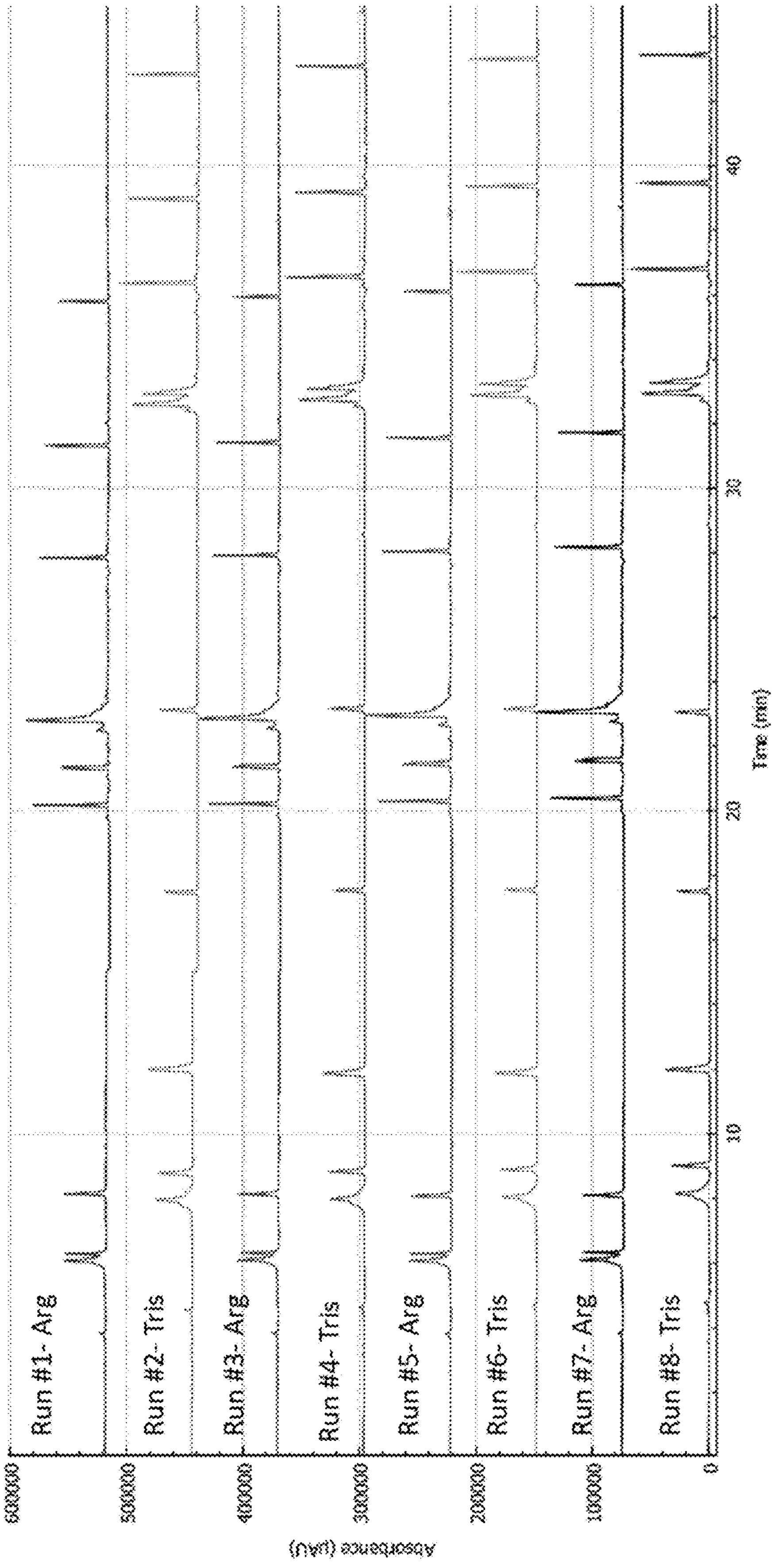
FIG. 2C shows a comparison of a cIEF separation according to an aspect of this disclosure of IgG with arginine (run #s 1,3,5,7) and Tris (run #s 2,4,6,8).

As shown in FIGS. 2A-2C, the pH gradient is wider between pI 7.0 and pI 9.5 in the cIEF sample with Tris. Additionally, multiple IgG isoforms are present when Tris is used in the cIEF sample as compared to arginine.

Figure 2D:
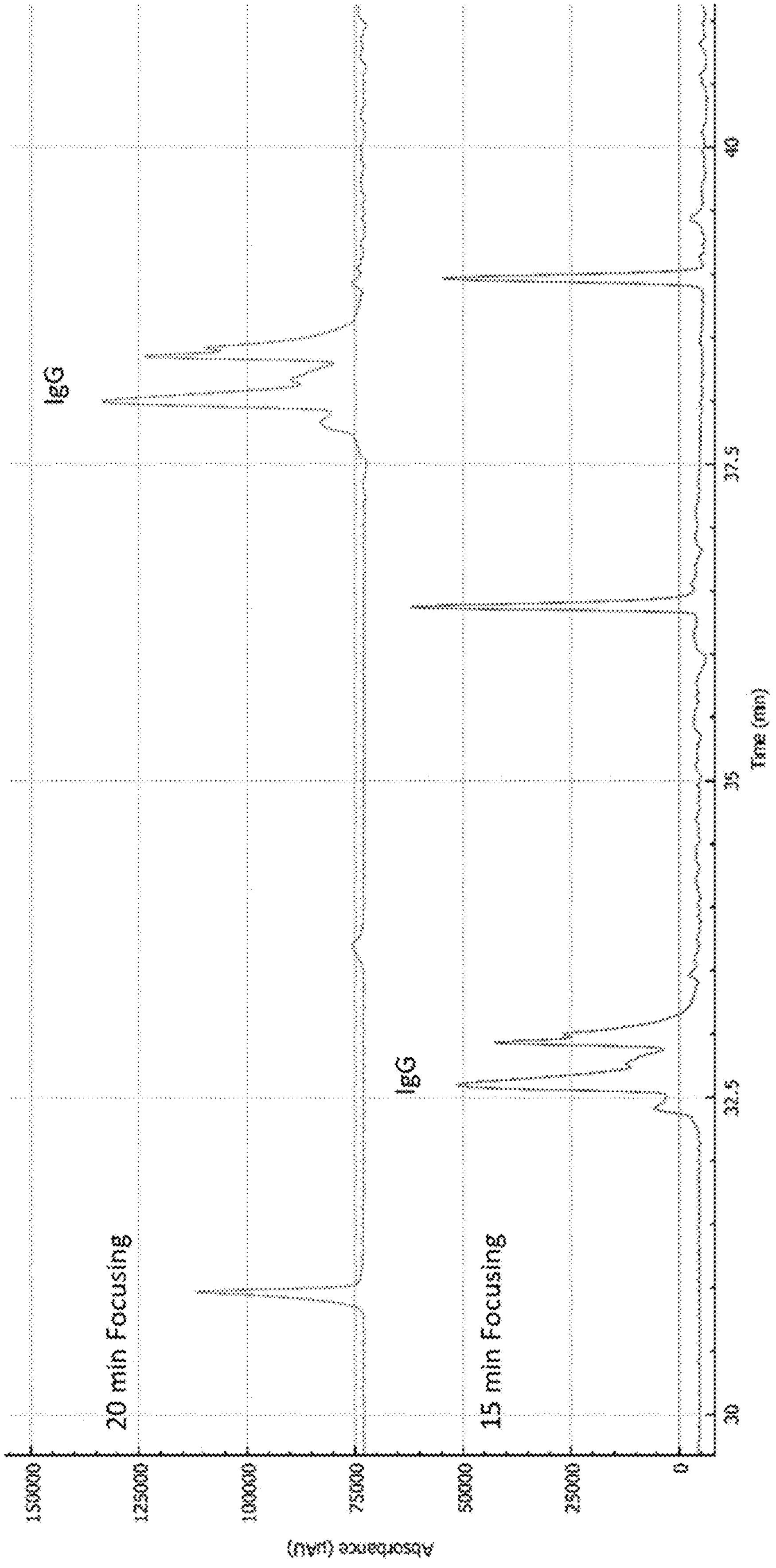
FIG. 2D shows a comparison of a cIEF separation according to an aspect of this disclosure of IgG using Tris and a 15 min (top graph) and 20 min (bottom graph) focusing at 25 kV.

The data in FIG. 2D is generated from cIEF separations of NIST IgG with 5 peptide pI markers using 15 min and 20 min Focusing at 25 kV using Tris. The NIST IgG profile is unaffected by the focusing time, providing further evidence that Tris results in an increase of pH gradient resolution above its pKa value and provides increased resolution for compounds with pI values between 7.0 and 9.5

Use of Bis-Tris to Modify a pH Gradient

Figure 3:
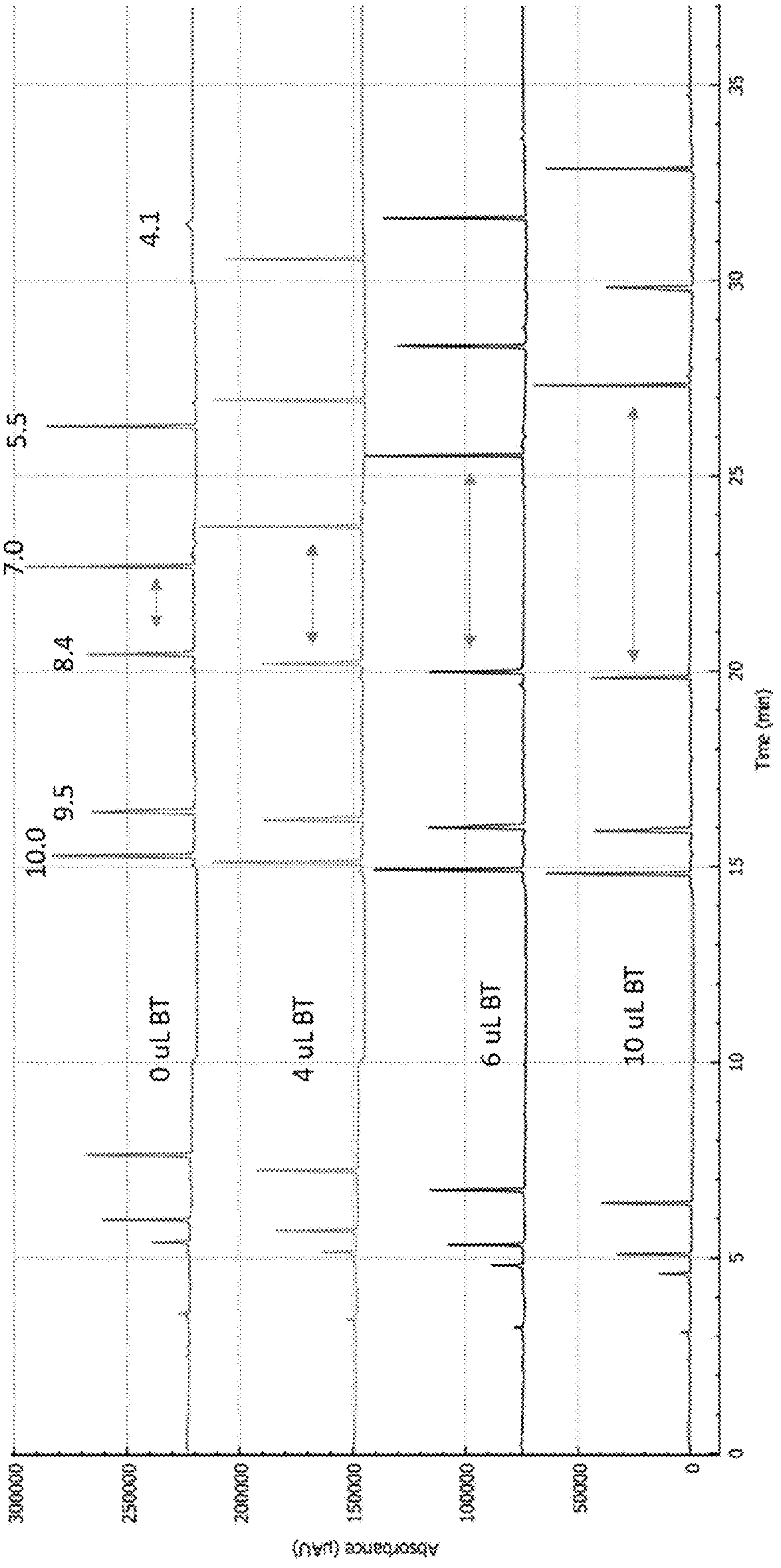
FIG. 3 shows a cIEF separation according to an aspect of this disclosure of 25 μL Arginine and various amounts of Bis-Tris (control (first graph), 4 μL (second graph), 6 μL (third graph), 10 μL (fourth graph)) in a cIEF composition in a 10 minute focusing at 25 kV.

Four cIEF samples were prepared by combining the following volumes 200 μL cIEF gel, 12 μL of Pharmalyte 3-10, 2.0 μL of each pI marker, and 25 μL of arginine with three different volumes of Bis-Tris (4 μL, 6 μL, 10 μL) and a control. The samples were separated using the exemplary method; Bis-Tris has a pKa value of 6.46 and increases resolution between pI 7.0 and pI 8.4. As shown in FIG. 3, the Bis-Tris focusing area forms between pI 7.0 and pI 8.4 and increases with increasing amounts of Bis-Tris added to the composition.

Use of Bis-Tris in a cIEF Separation of Protein Isoforms

Figure 4A:
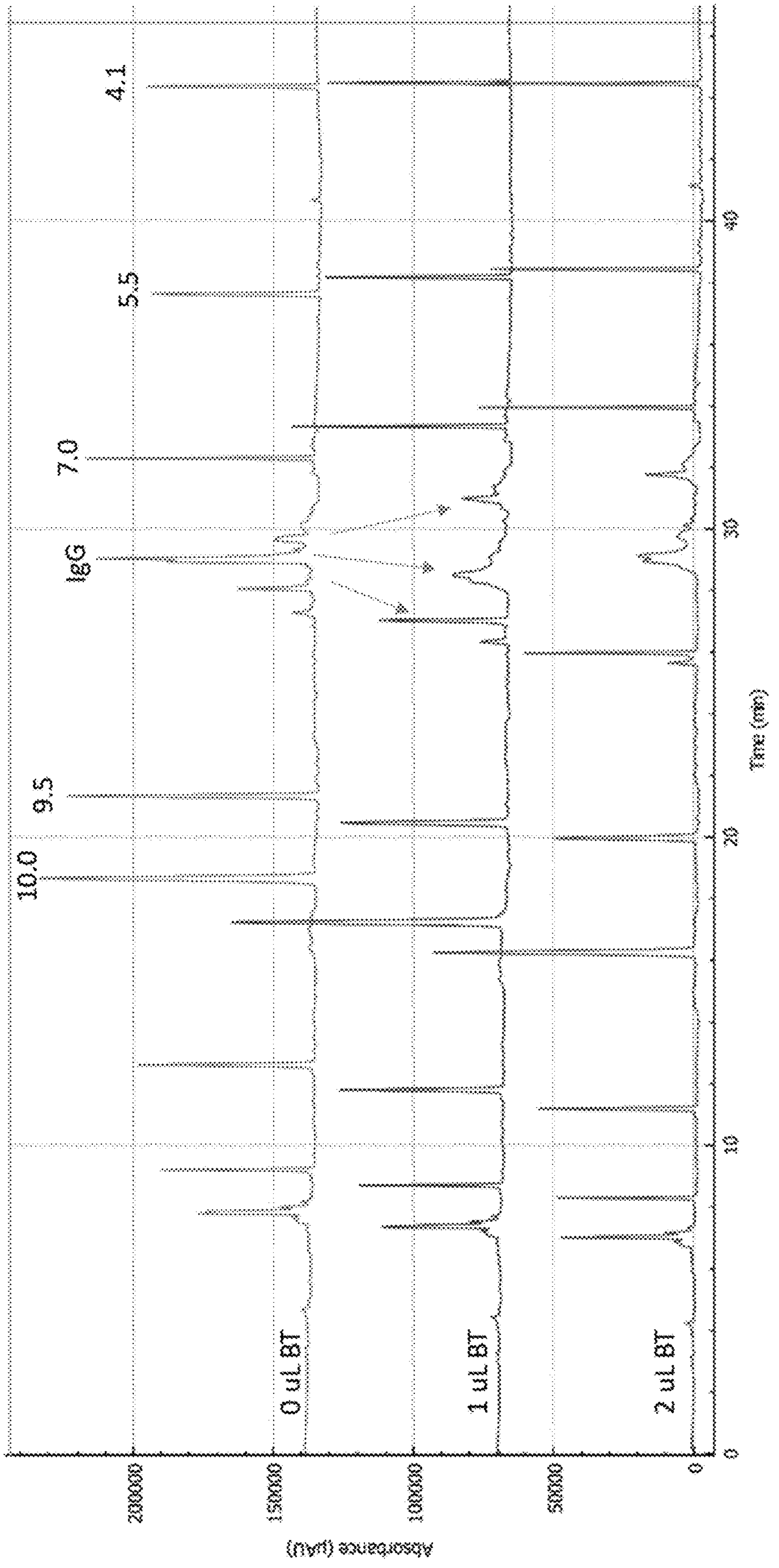
FIG. 4A shows a cIEF separation according to an aspect of this disclosure of 25 μL Arginine and various amounts of Bis-Tris (control (first graph), 1 μL (second graph), 2 μL (third graph)) in a cIEF composition with a 17.5 minute focusing at 25 kV.
Figure 4B:
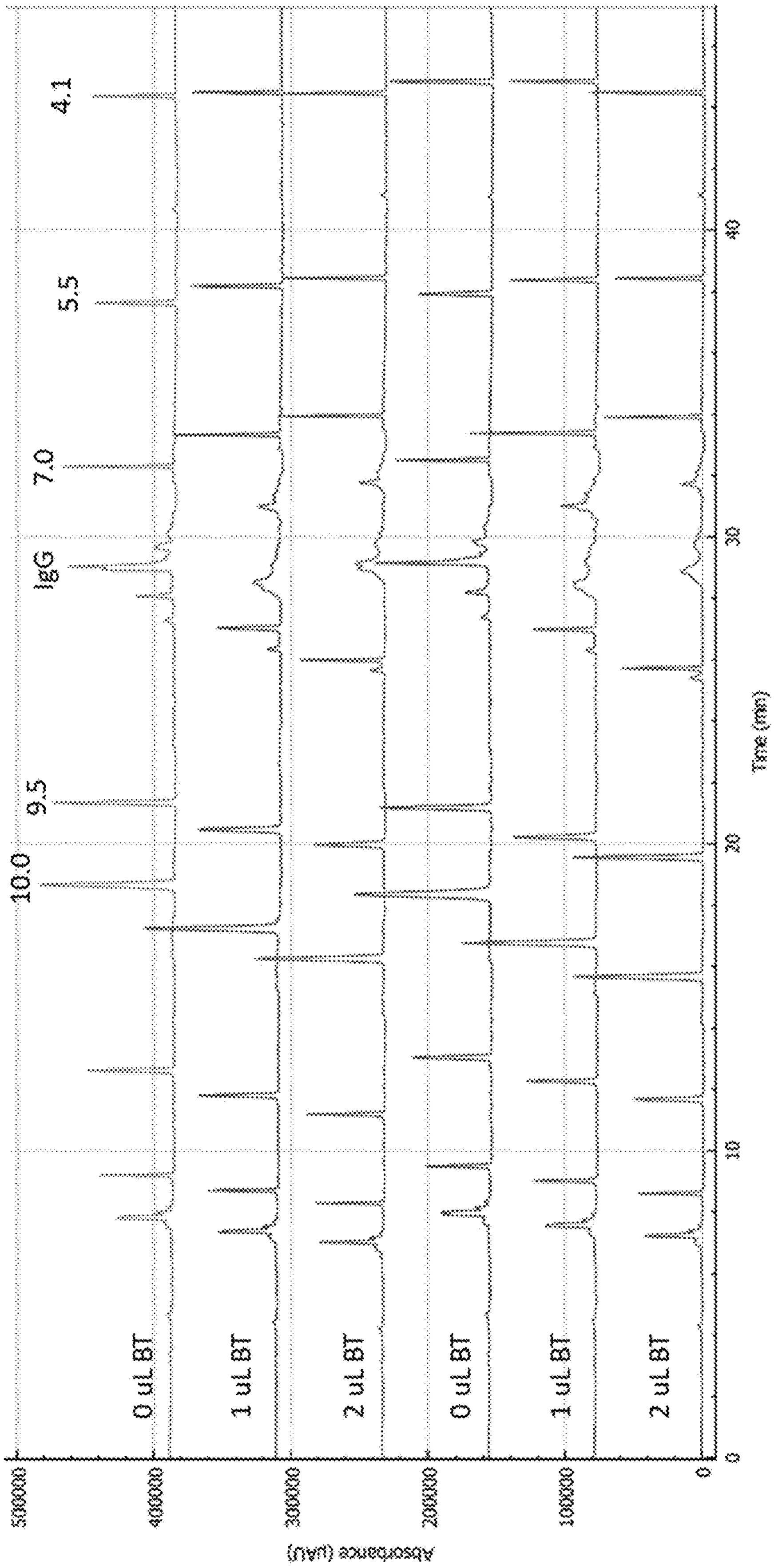
FIG. 4B shows a cIEF separation according to an aspect of this disclosure of 25 μL Arginine and various amounts of Bis-Tris (control, 1 μL, 2 μL) in a cIEF composition with a 17.5 minute focusing at 25 kV.
Figure 4C:
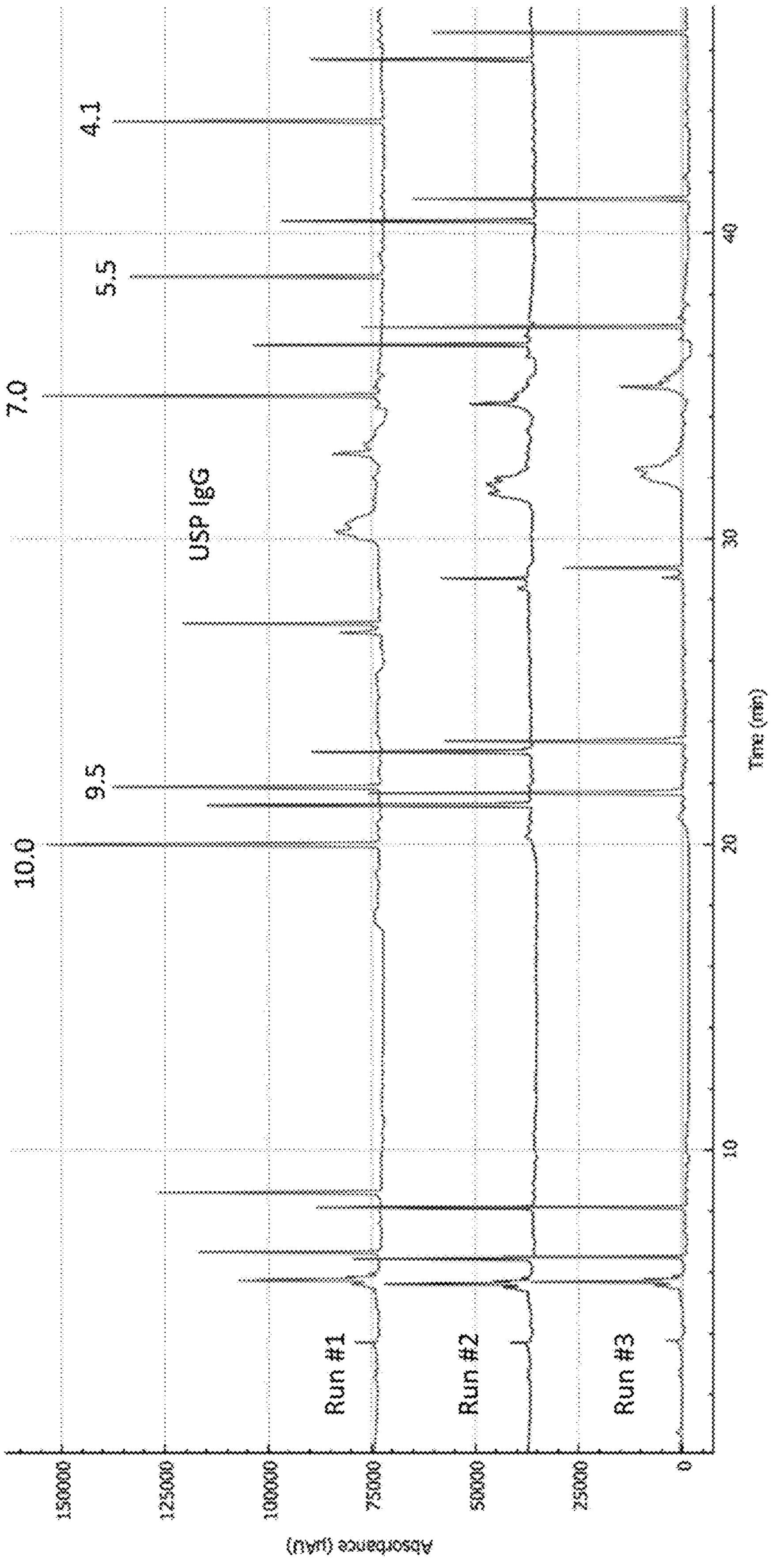
FIG. 4C shows a cIEF separation according to an aspect of this disclosure of 25 μL Arginine 2 μL Bis-Tris in a cIEF composition with a 17.5 minute focusing at 25 kV.

Three cIEF samples were prepared by combining the following volumes 200 μL cIEF gel, 12 μL of Pharmalyte 3-10, 2.0 μL of each pI marker, and 25 μL of arginine with three different volumes of Bis-Tris (1 μL, 2 μL) and a control. The samples were separated using the exemplary method. As shown in FIG. 4A and FIG. 4B, the pH gradient is wider between pI 7.0 and pI 8.4, allowing for improved resolution of IgG as compared to a control. FIG. 4C shows the reproducibility of the method using 2 μL and a 17.5 minute focusing at 25 kV. The data shows that Bis-Tris results in an increase of pH gradient for compounds with pI values between 7.0 and 8.4.

All features disclosed in the specification, including the claims, abstracts, and drawings, and all the steps in any method or process disclosed, may be combined in any combination, except combinations where at least some of such features and/or steps are mutually exclusive. Each feature disclosed in the specification, including the claims, abstract, and drawings, can be replaced by alternative features serving the same, equivalent or similar purpose, unless expressly stated otherwise. Thus, unless expressly stated otherwise, each feature disclosed is one example only of a generic series of equivalent or similar features.

It will be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for analyzing at least one analyte, the method comprising:
- introducing a composition into a separation channel, wherein the composition comprises at least one carrier ampholyte, an amine buffer present in an amount effective to produce a non-linear pH gradient, and at least one analyte of interest;
- applying an electric field across the separation channel to establish the non-linear pH gradient and separating the composition via isoelectric focusing, generating at least one focused analyte peak;
- mobilizing the at least one focused analyte peak; and
- wherein the presence of the amine buffer and the resulting non-linear pH gradient provide improved separation of the at least one analyte relative to that attained in a method which does not comprise the amine buffer.

2. The method of claim 1, wherein the amine buffer is present in an amount effective to produce a shallow pH gradient.

3. The method of claim 1, wherein the amine buffer has a pKa of about 6.0 to about 8.5.

4. The method of claim 1, wherein the amine buffer is selected from the group consisting of Tris, Bis-Tris, HEPES, MES, PIPES, TES, dimethylamine, and combinations thereof.

5. The method of claim 1, wherein the at least one analyte has a pI of between about 7.0 and about 9.5.

6. The method of claim 1, further comprising introducing a polymer solution, an anodic stabilizer, a cathodic stabilizer, and/or a pI marker into the separation channel.

7. The method of claim 6, wherein the anodic stabilizer comprises a carboxylic acid.

8. The method of claim 7, wherein the anodic stabilizer comprises acetic acid or iminodiacetic acid and/or wherein the cathodic stabilizer comprises arginine.

9. The method of claim 6, wherein the at least one focused analyte peak is mobilized using pressure or a chemical mobilizer, wherein the anodic stabilizer is used as a chemical mobilizer.

10. The method of claim 1, wherein the method further comprises imaging the separation channel or a portion thereof during or after the isoelectric focusing separation and/or mobilization, wherein imaging the separation channel or a portion thereof is used to generate image data.

11. The method of claim 10, further comprising expelling the at least one mobilized analyte peak into a mass spectrometer and generating mass spectrometry data.

12. The method of claim 11, further comprising correlating the image data with mass spectrometry data for the at least one focused analyte.

13. The method of claim 11, wherein the method further comprises generating a corresponding set of values from the image data and/or mass spectrometry data, wherein the corresponding set of values is used to generate a calibration curve.

14. The method of claim 13, wherein the calibration curve is a linear or non-linear calibration curve.

15. The method of claim 13, wherein the calibration curve is used to determine the pI value of an unknown analyte.

* * * * *